United States Patent [19]  
Greene et al.

[11] Patent Number: 4,826,765  
[45] Date of Patent: May 2, 1989

[54] YEAST STRAINS GENETICALLY ENGINEERED TO PRODUCE WHEAT GLUTEN PROTEINS

[75] Inventors: Frank C. Greene, Berkeley, Calif.; John I. Stiles, Kaneohe, Hi.; John D. Neill, Ames, Iowa; Olin D. Anderson, Pleasant Hill, Calif.; James C. Litts, Corvallis, Oreg.

[73] Assignees: The United States of America as represented by the Secretary of the Agriculture, Washington, D.C.; The University of Hawaii, Honolulu, Hi.

[21] Appl. No.: 922,616

[22] Filed: Oct. 24, 1986

[51] Int. Cl.$^4$ .................. C12P 21/00; C12P 21/02; C12N 15/00; C12N 1/20
[52] U.S. Cl. ........................ 435/68; 435/70; 435/91; 435/172.3; 435/251; 435/255; 435/256; 435/320; 435/252.33; 935/12; 935/28; 935/37; 935/69; 935/60
[58] Field of Search ............. 435/68, 70, 172.3, 255, 435/320; 536/27; 935/12, 28, 37, 69, 60, 11

[56] References Cited

PUBLICATIONS

Hanna et al Gene vol 30 1984 pp. 247–250 "Construction of a family of universal expression plasmid vectors".
Harberd et al Mol Gen Genet, vol. 198 pp. 231–242 "Analysis of the yliadin multigene loci in bread wheat using nullisomic–tetrasomic lines".
Rymond et al Biol Abst. vol. 78 No. 11050 1983 "The Expression in yeast of the Escherichia coli Gal-K gene in CYC-1 Gal-K Fusion Plasmids".
Zaret et al Biol Abst vol. 79 No. 13069 1984 "Mututionally altered 3 ends of yeast CYG1 Messenger RNA Affect Transcript Stability and Translationed Efficiency".
Kuo et al Mol Cell Biol vol. 3 (10) pp. 1730–1737 Oct. 1983 "Cloning of Saccharomyces cerevisiae DNA replication genes: . . . ".
Bartels et al Gene vol. 35 pp. 159–167 1985 "Synthesis of a wheat storage protein in Escherichia coli . . . ".
M. Kozak, "Possible Role of Flanking Nucleotides in Recognition of the AUG Initiator Codon by Eukaryotic Ribosomes," Nucleic Acids Research 9:5233–5252 (1981).
M. Kozak, "Mechanism of mRNA Recognition by Eukaryotic Ribosomes During Initiation of Protein Synthesis," Current Topics in Microbiology and Immunology 93 81–123 (1981).
J. Stiles et al., "DNA Sequence of a Mutation in the Leader Region of the Yeast Iso-1-cytochrome c mRNA," Cell 25:277–284 (1981).

(List continued on next page.)

Primary Examiner—Robin Teskin
Attorney, Agent, or Firm—M. Howard Silverstein; Margaret A. Connor

[57] ABSTRACT

A strain of yeast Saccharomyces cerevisiae has been developed which, when grown under defined culture conditions, will produce protein indistinguishable from wheat gluten protein. This new yeast strain was developed by introducing a specially constructed autonomously replicating extrachromosomal genetic element, gluten plasmid pAY31, into the parent yeast strain. This plasmid is a circular DNA molecule, constructed by enzymic fusion of the following elements: (1) the E. coli plasmid pUC8 wherein the EcoRI site has been removed; (2) the autonomously replicating yeast sequence ARS1; (3) the yeast URA3 gene; (4) a modified yeast iso-1-cytochromic gene retaining the promoter region and transcription termination sequence, and wherein the protein coding sequences have been deleted and replaced with a synthetic EcoRI restriction site, the site at which the wheat gluten protein gene is cloned; and (5) a fragment of a wheat gluten protein gene which includes the amino acid coding region, translation initiation and termination sequence, and short flanking nucleotide sequences, but excludes transcription initiation and termination sequences. Wheat gluten protein synthesized by the new yeast strain can be used to supplement wheat and non-wheat flours for baked products and for use in diagnosis and treatment of illness in humans caused by wheat gluten proteins.

13 Claims, 12 Drawing Sheets

PUBLICATIONS

Baim et al., "Rules of Translation: Studies with Altered Forms of the Yeast CYC1 Gene," In: *Sequence Specificity in Transcription and Translation,* pp. 351–362 (1985).

P. M. Sharp, T. M. f. Tuohy, and K. R. Mosurski, "Codon Usage in Yeast: Cluster Analysis Clearly Differentiates Highly and Lowly Expressed Genes," *Nucleic Acids Research* 14:5125–5143 (1986).

G. Ammerer, "Expression of Genes in Yeast Using the ADCI Promoter," *Methods in Enzymology,* vol. 101, *Recombinant DNA,* Part C, Ed. R. Wu et al., pp. 192–201 (1983).

G. A. Bitter et al., "Expression and Secretion Vectors for Yeast," *Methods in Enzymology,* vol. 153, *Recombinant DNA,* Part D. Ed. R. Wu and L. Grossman, Academic Press, Inc., pp. 516–517 (1987).

J. D. Neill and J. I. Stiles, "Construction of a Novel Shuttle Vector for the Expression and Selection of Foreign Genes in Yeast," (Abstract) Annual Meeting of the American Society of Plant Physiologists, Aug. 12–17, 1984.

S. J. Rothstein, C. M. Lazarus, W. E. Smith, D. C. Baulcombe, and A. A. Gatenby, "Secretion of a Wheat α-Amylase Expressed in Yeast," *Nature* 308: 662–665 (1984).

A. J. Brake et al., "α-Factor-directed Synthesis and Secretion of Mature Foreign Proteins in *Saccharomyces cerevisiae,*" *Proc. Natl. Acad. Sci.* USA 81: 4642–4646 (1984).

J. Oberto and J. Davison, "Expression of Chicken Egg White Lysozyme by *Saccharomyces cerevisiae,*" *Gene* 40: 57–65 (1985).

N. Fujita, N. Nelson, T. D. Fox, T. Claudio, J. Linstrom, H. Riezman and G. P. Hess, "Biosynthesis of the *Torpedo californica* Acetylcholine Receptor α Subunit in Yeast," *Science* 231:1284–1287 (1986).

I. Coraggio, C. Compagno, E. Martegani, B. J. Ranzi, E. Sala, L. Alberghina, and A. Viotti, "Transcription and Expression of Zein Sequences in Yeast Under Natural Plant or Yeast Promoters," *The EMBO Journal* 5(3):459–465 (1986).

O. D. Anderson, J. C. Litts, M.-F. Gautier, and F. C. Greene, "Nucleic Acid Sequence and Chromosome Assignment of a Wheat Storage Protein Gene," *Nucleic Acids Research* 12(21): 8129–8144 (1984).

H Ito, Y. Fukuda, K. Murata, and A. Kimura, "Transformation of Intact Yeast Cells Treated with Alkali Cations," *Journal of Bacteriology* 153:163–168 (1983).

LISTING OF THE SEQUENCE PAY31

PAY31 IS THE UPPER SEQUENCE

```
         10        20        30        40        50        60        70        80
CTGCCTCGCGCGTTTCGGTGATGACGGTGAAAACCTCTGACACATGCAGCTCCCGGAGACGGTCACAGCTTGTCTGTAAG
GACGGAGCGCGCAAAGCCACTACTGCCACTTTTGGAGACTGTGTACGTCGAGGGCCTCTGCCAGTGTCGAACAGACATTC 90       100       110       120       130       140       150       160
CGGATGCCGGGAGCAGACAAGCCCGTCAGGGCGCGTCAGCGGGTGTTGGCGGGTGTCGGGGCGCAGCCATGACCCAGTCA
GCCTACGGCCCTCGTCTGTTCGGGCAGTCCCGCGCAGTCGCCCACAACCGCCCACAGCCCCGCGTCGGTACTGGGTCAGT 170       180       190       200       210       220       230       240
CGTAGCGATAGCGGAGTGTACTGGCTTAACTATGCGGCATCAGAGCAGATTGTACTGAGAGTGCACCATATGCGGTGTGA
GCATCGCTATCGCCTCACATGACCGAATTGATACGCCGTAGTCTCGTCTAACATGACTCTCACGTGGTATACGCCACACT 250       260       270       280       290       300       310       320
AATACCGCACAGATGCGTAAGGAGAAAATACCGCATCAGGCGCCATTCGCCATTCAGGCTGCGCAACTGTTGGGAAGGGC
TTATGGCGTGTCTACGCATTCCTCTTTTATGGCGTAGTCCGCGGTAAGCGGTAAGTCCGACGCGTTGACAACCCTTCCCG 330       340       350       360       370       380       390       400
GATCGGTGCGGGCCTCTTCGCTATTACGCCAGCTGGCGAAAGGGGGATGTGCTGCAAGGCGATTAAGTTGGGTAACGCCA
CTAGCCACGCCCGGAGAAGCGATAATGCGGTCGACCGCTTTCCCCCTACACGACGTTCCGCTAATTCAACCCATTGCGGT 410       420       430       440       450       460       470       480
GGGTTTTCCCAGTCACGACGTTGTAAAACGACGGCCAGTGCCAAGCTTTTTCTTTCCAATTTTTTTTTTTTCGTCATTAT
CCCAAAAGGGTCAGTGCTGCAACATTTTGCTGCCGGTCACGGTTCGAAAAAGAAAGGTTAAAAAAAAAAAAGCAGTAATA 490       500       510       520       530       540       550       560
AAAAATCATTACGACCGAGATTCCCGGGTAATAACTGATATAATTAAATTGAAGCTCTAATTTGTGAGTTTAGTATACAT
TTTTTAGTAATGCTGGCTCTAAGGGCCCATTATTGACTATATTAATTTAACTTCGAGATTAAACACTCAAATCATATGTA 570       580       590       600       610       620       630       640
GCATTTACTTATAATACAGTTTTTTAGTTTTGCTGGCCGCATCTTCTCAAATATGCTTCCCAGCCTGCTTTTCTGTAACG
CGTAAATGAATATTATGTCAAAAAATCAAAACGACCGGCGTAGAAGAGTTTATACGAAGGGTCGGACGAAAAGACATTGC 650       660       670       680       690       700       710       720
TTCACCCTCTACCTTAGCATCCCTTCCCTTTGCAAATAGTCCTCTTCCAACAATAATAATGTCAGATCCTGTAGAGACCA
AAGTGGGAGATGGAATCGTAGGGAAGGGAAACGTTTATCAGGAGAAGGTTGTTATTATTACAGTCTAGGACATCTCTGGT 730       740       750       760       770       780       790       800
CATCATCCACGGTTCTATACTGTTGACCCAATGCGTCTCCCTTGTCATCTAAACCCACACCGGGTGTCATAATCAACCAA
GTAGTAGGTGCCAAGATATGACAACTGGGTTACGCAGAGGGAACAGTAGATTTGGGTGTGGCCCACAGTATTAGTTGGTT 810       820       830       840       850       860       870       880
TCGTAACCTTCATCTCTTCCACCCATGTCCTCTTGAGCAATAAAGCCGATAACAAAATCTTTGTCGCTCTTCGCAATGTC
AGCATTGGAAGTAGAGAAGGTGGGTACAGGAGAACTCGTTATTTCGGCTATTGTTTTAGAAACAGCGAGAAGCGTTACAG 890       900       910       920       930       940       950       960
AACAGTACCCTTAGTATATTCTCCAGTAGATAGGGAGCCCTTGCATGACAATTCTGCTAACATCAAAAGGCCTCTAGGTT
TTGTCATGGGAATCATATAAGAGGTCATCTATCCCTCGGGAACGTACTGTTAAGACGATTGTAGTTTTCCGGAGATCCAA 970       980       990      1000      1010      1020      1030      1040
CCTTTGTTACTTCTTCTGCCGCCTGCTTCAAACCGCTAACAATACCTGGGCCCACCACACCGTGTGCATTCGTAATGTCT
GGAAACAATGAAGAAGACGGCGGACGAAGTTTGGCGATTGTTATGGACCCGGGTGGTGTGGCACACGTAAGCATTACAGA 1050      1060      1070      1080      1090      1100      1110      1120
GCCCATTCTGCTATTCTGTATACACCCGCAGAGTACTGCAATTTGACTGTATTACCAATGTCAGCAAATTTTCTGTCTTC
CGGGTAAGACGATAAGACATATGTGGGCGTCTCATGACGTTAAACTGACATAATGGTTACAGTCGTTTAAAAGACAGAAG
```

FIG. 4A

```
         1130      1140      1150      1160      1170      1180      1190      1200
GAAGAGTAAAAAATTGTACTTGGCGGATAATGCCTTTAGCGGCTTAACTGTGCCCTCCATGGAAAAATCAGTCAAGATAT
CTTCTCATTTTTTAACATGAACCGCCTATTACGGAAATCGCCGAATTGACACGGGAGGTACCTTTTTAGTCAGTTCTATA 1210      1220      1230      1240      1250      1260      1270      1280
CCACATGTGTTTTTAGTAAACAAATTTTGGGACCTAATGCTTCAACTAACTCCAGTAATTCCTTGGTGGTACGAACATCC
GGTGTACACAAAAATCATTTGTTTAAAACCCTGGATTACGAAGTTGATTGAGGTCATTAAGGAACCACCATGCTTGTAGG 1290      1300      1310      1320      1330      1340      1350      1360
AATGAAGCACACAAGTTTGTTTGCTTTTCGTGCATGATATTAAATAGCTTGGCAGCAACAGGACTAGGATGAGTAGCAGC
TTACTTCGTGTGTTCAAACAAACGAAAAGCACGTACTATAATTTATCGAACCGTCGTTGTCCTGATCCTACTCATCGTCG 1370      1380      1390      1400      1410      1420      1430      1440
ACGTTCCTTATATGTAGCTTTCGACATGATTTATCTTCGTTTCCTGCAGGTTTTTGTTCTGTGCAGTTGGGTTAAGAATA
TGCAAGGAATATACATCGAAAGCTGTACTAAATAGAAGCAAAGGACGTCCAAAAACAAGACACGTCAACCCAATTCTTAT 1450      1460      1470      1480      1490      1500      1510      1520
CTGGGCAATTTCATGTTTCTTCAACACTACATATGCGTATATATACCAATCTAAGTCTGTGCTCCTTCCTTCGTTCTTCC
GACCCGTTAAAGTACAAAGAAGTTGTGATGTATACGCATATATATGGTTAGATTCAGACACGAGGAAGGAAGCAAGAAGG 1530      1540      1550      1560      1570      1580      1590      1600
TTCTGTTCGGAGATTACCGAATCAAAAAAATTTCAAAGAAACCGAAATCAAAAAAAAGAATAAAAAAAAAAATGATGAATT
AAGACAAGCCTCTAATGGCTTAGTTTTTTTAAAGTTTCTTTGGCTTTAGTTTTTTTTCTTATTTTTTTTTACTACTTAA 1610      1620      1630      1640      1650      1660      1670      1680
GAATTGAAAAGCTTGGCTGCAGGTCGACAATCTTACATGGTCTACCTTTGATGACAACGAAACCATTCTTTCTCAAGGCA
CTTAACTTTTCGAACCGACGTCCAGCTGTTAGAATGTACCAGATGGAAACTACTGTTGCTTTGGTAAGAAAGAGTTCCGT 1690      1700      1710      1720      1730      1740      1750      1760
GAACATTGCATTGGGTAGGTGGCGGAGGCACCAGCGTCAGCATTTTCAAAGGTTGTGTTCTTCGTCAGACATGTTTTAGT
CTTGTAACGTAACCCATCCACCGCCTCCGTGGTCGCAGTCGTAAAAGTTTCCAACACAAGAAGCAGTCTGTACAAAATCA 1770      1780      1790      1800      1810      1820      1830      1840
GTGTGAATGAAATAGGTGTATGTTTTCTTTTGCAGACAATAATTAGGAACAAGGTAAGGGAACTAAAGTGTAGAATAAGA
CACACTTACTTTATCCACATACAAAAGAAAACGTCTGTTATTAATCCTTGTTCCATTCCCTTGATTTCACATCTTATTCT 1850      1860      1870      1880      1890      1900      1910      1920
ATTAAAAAAGAAGAACAAGTTGAAAGGCAAGTTGAAATTTCAAGAAAAAAGTCAATTGAAGTACAGTAAATTGACCTGAA
TAATTTTTTCTTCTTGTTCAACTTTCCGTTCAACTTTAAAGTTCTTTTTTCAGTTAACTTCATGTCATTTAACTGGACTT 1930      1940      1950      1960      1970      1980      1990      2000
TATATCTGAGTTCCGAGCAACAATGAGTTTACCGAAGAGAACAATGGAATAGGAAACTTTGAACGAAGAAAGGAAAGCAG
ATATAGACTCAAGGCTCGTTGTTACTCAAATGGCTTCTCTTGTTACCTTATCCTTTGAAACTTGCTTCTTTCCTTTCGTC 2010      2020      2030      2040      2050      2060      2070      2080
GAAAGGAAAAAATTTTTAGGCTCGAGAACAATAGGGCAAAAAAACAGGCAACGAACGAACAAATGGAAAAACGAAAAAAA
CTTTCCTTTTTTAAAAATCCGAGCTCTTGTTATCCCGTTTTTTTGTCCGTTGCTTGCTTGTTTACCTTTTTGCTTTTTT 2090      2100      2110      2120      2130      2140      2150      2160
AAAAAACACAGAAAAGAATGCAGAAAGTTGTAAACTGAAAAAAAAAAAAAAAAAAGGTGAACACAGGAAAAAAAATAAAA
TTTTTTGTGTCTTTTCTTACGTCTTTCAACATTTGACTTTTTTTTTTTTTTTTTTCCACTTGTGTCCTTTTTTTATTTT 2170      2180      2190      2200      2210      2220      2230      2240
AAAAAAAAAAGGAGGACGAAACAAAAAAGTGAAAAAAAATGAAAATTTTTTGGAAAACCAAGAAATGAATTATATTTC
TTTTTTTTTTCCTCCTGCTTTGTTTTTTCACTTTTTTTACTTTTAAAAAAACCTTTTGGTTCTTTACTTAATATAAAG
```

FIG. 4B

```
        2250      2260      2270      2280      2290      2300      2310      2320
CGTGTGAGACGACATCGTCGAATATGATTCAGGGTAACAGTATTTATGTAATCAATTTCCTACCTGAATCTAAAATTCCC
GCACACTCTGCTGTAGCAGCTTATACTAAGTCCCATTGTCATAAATACATTAGTTAAAGGATGGACTTAGATTTTAAGGG 2330      2340      2350      2360      2370      2380      2390      2400
GGGAGCAAGATCAAGATGTTTTCACCGATCTTTCCGGTCTCTTTGGCCGGGGTTTACGGACGATGACCGAAGACCAAGCG
CCCTCGTTCTAGTTCTACAAAAGTGGCTAGAAAGGCCAGAGAAACCGGCCCCAAATGCCTGCTACTGGCTTCTGGTTCGC 2410      2420      2430      2440      2450      2460      2470      2480
CCAGCTCATTTGGCGAGCGTTGGTTGGTGGATCAAGCCCACGCGTAGGCAATCCTCGAGCAGATCCGCCAGGCGTGTATA
GGTCGAGTAAACCGCTCGCAACCAACCACCTAGTTCGGGTGCGCATCCGTTAGGAGCTCGTCTAGGCGGTCCGCACATAT 2490      2500      2510      2520      2530      2540      2550      2560
TAGCGTGGATGGCCAGGCAACTTTAGTGCTGACACATACAGGCATATATATATGTGTGCGACGACACATGATCATATGGC
ATCGCACCTACCGGTCCGTTGAAATCACGACTGTGTATGTCCGTATATATATACACACGCTGCTGTGTACTAGTATACCG 2570      2580      2590      2600      2610      2620      2630      2640
ATGCATGTGCTCTGTATGTATATAAAACTCTTGTTTTCTTCTTTTCTCTAAATATTCTTTCCTTATACATTAGGTCCTTT
TACGTACACGAGACATACATATATTTTGAGAACAAAAGAAGAAAAGAGATTTATAAGAAAGGAATATGTAATCCAGGAAA 2650      2660      2670      2680      2690      2700      2710      2720
GTAGCATAAATTACTATACTTCTATAGACACGCAAACACAAATACACACAGGAATTCGGTCAATACAAATCCACCATGAA
CATCGTATTTAATGATATGAAGATATCTGTGCGTTTGTGTTTATGTGTGTCCTTAAGCCAGTTATGTTTAGGTGGTACTT 2730      2740      2750      2760      2770      2780      2790      2800
GACCTTTCTCATCCTTGTCCTCCTTGCTATTGTGGCGACCACCGCCACAACTGCAGTTAGATTTCCAGTGCCACAATTGC
CTGGAAAGAGTAGGAACAGGAGGAACGATAACACCGCTGGTGGCGGTGTTGACGTCAATCTAAAGGTCACGGTGTTAACG 2810      2820      2830      2840      2850      2860      2870      2880
AGCCACAAAATCCATCTCAGCAACAGCCACAAGAGCAAGTTCCATTGGTACAACAACAACAATTTCTAGGGCAGCAACAA
TCGGTGTTTTAGGTAGAGTCGTTGTCGGTGTTCTCGTTCAAGGTAACCATGTTGTTGTTGTTAAAGATCCCGTCGTTGTT 2890      2900      2910      2920      2930      2940      2950      2960
CCATTTCCACCACAACAACCATATCCACAGCCGCAACCATTTCCATCACAACTACCATATCTGCAGCTGCAACCATTTCC
GGTAAAGGTGGTGTTGTTGGTATAGGTGTCGGCGTTGGTAAAGGTAGTGTTGATGGTATAGACGTCGACGTTGGTAAAGG 2970      2980      2990      3000      3010      3020      3030      3040
GCAGCCGCAACTACCATATTCACAGCCACAACCATTTCGACCACAACAACCATATCCACAACCGCAACAACAGTATTCGC
CGTCGGCGTTGATGGTATAAGTGTCGGTGTTGGTAAAGCTGGTGTTGTTGGTATAGGTGTTGGCGTTGTTGTCATAAGCG 3050      3060      3070      3080      3090      3100      3110      3120
AACCACAACAACCAATTTCACAGCAGCAGCAGCAGCAGCAGCAGCAACAACAACAACAACAACAACAACAAATCCTT
TTGGTGTTGTTGGTTAAAGTGTCGTCGTCGTCGTCGTCGTCGTCGTCGTTGTTGTTGTTGTTGTTGTTTAGGAA 3130      3140      3150      3160      3170      3180      3190      3200
CAACAAATTTTGCAACAACAACTGATTCCATGCATGGATGTTGTATTGCAGCAACACAACATAGCGCATGGAAGATCACA
GTTGTTTAAAACGTTGTTGTTGACTAAGGTACGTACCTACAACATAACGTCGTTGTGTTGTATCGCGTACCTTCTAGTGT 3210      3220      3230      3240      3250      3260      3270      3280
AGTTTTGCAACAAAGTACTTACCAGCTGTTGCAAGAATTGTGTTGTCAACACCTATGGCAGATCCCTGAGCAGTCGCAGT
TCAAAACGTTGTTTCATGAATGGTCGACAACGTTCTTAACACAACAGTTGTGGATACCGTCTAGGGACTCGTCAGCGTCA 3290      3300      3310      3320      3330      3340      3350      3360
GCCAGGCCATCCTCAAAGTTGTTCATGCTATTATTCTGCATCAACAACAAAAACAACAACAACAACCATCGAGCCAGGTC
CGGTCCGGTAGGAGTTTCAACAAGTACGATAATAAGACGTAGTTGTTGTTTTTGTTGTTGTTGTTGGTAGCTCGGTCCAG
```

FIG. 4C

```
       3370      3380      3390      3400      3410      3420      3430      3440
TCCTTCCAACAGCCTCTGCAACAATATCCATTAGGCCAGGGCTCCTTCCGGCCATCTCAGCAAAACCCACAGGCCCAGGG
AGGAAGGTTGTCGGAGACGTTGTTATAGGTAATCCGGTCCCGAGGAAGGCCGGTAGAGTCGTTTTGGGTGTCCGGGTCCC 3450      3460      3470      3480      3490      3500      3510      3520
CTCTGTCCAGCCTCAACAACTGCCCCAGTTCGAGGAAATAAGGAACCTAGCGCTACAGACGCTACCTGCAATGTGCAATG
GAGACAGGTCGGAGTTGTTGACGGGGTCAAGCTCCTTTATTCCTTGGATCGCGATGTCTGCGATGGACGTTACACGTTAC 3530      3540      3550      3560      3570      3580      3590      3600
TCTACATCCCTCCATATTGCACCATCGCGCCATTTGGCATCTTCGGTACTAACTGAGAAGAAAATAGCTCTAGTACTAGA
AGATGTAGGGAGGTATAACGTGGTAGCGCGGTAAACCGTAGAAGCCATGATTGACTCTTCTTTTATCGAGATCATGATCT 3610      3620      3630      3640      3650      3660      3670      3680
TATATGAAACACCGTTTTCTCAGTCCATGGGGAATTCCCTTCCTTTGTCGATATCATGTAATTAGTTATGTCACGCTTAC
ATATACTTTGTGGCAAAAGAGTCAGGTACCCCTTAAGGGAAGGAAACAGCTATAGTACATTAATCAATACAGTGCGAATG 3690      3700      3710      3720      3730      3740      3750      3760
ATTCACGCCCTCCCCCCACATCCGCTCTAACCGAAAAGGAAGGAGTTAGACAACCTGAAGTCTAGGTCCCTATTTATTTT
TAAGTGCGGGAGGGGGGTGTAGGCGAGATTGGCTTTTCCTTCCTCAATCTGTTGGACTTCAGATCCAGGGATAAATAAAA 3770      3780      3790      3800      3810      3820      3830      3840
TTTATAGTTATGTTAGTATTAAGAACGTTATTTATATTTCAAATTTTTCTTTTTTTCTGTACAGACGCGTGTACGCATG
AAATATCAATACAATCATAATTCTTGCAATAAATATAAAGTTTAAAAAGAAAAAAAAGACATGTCTGCGCACATGCGTAC 3850      3860      3870      3880      3890      3900      3910      3920
TAACATTATACTGAAAACCTTGCTTGAGAAGGTTTTGGGACGCTCGAAGGCTTTAATTTGCAAGCTTACATTTATGTTA
ATTGTAATATGACTTTTGGAACGAACTCTTCCAAAACCCTGCGAGCTTCCGAAATTAAACGTTCGAATGTAAAATACAAT 3930      3940      3950      3960      3970      3980      3990      4000
GCTGGTGGACTGACGCCAGAAAATGTTGGTGATGCGCTTAGATTAAATGGCGTTATTGGTGTTGATGTAAGCGGAGGTGT
CGACCACCTGACTGCGGTCTTTTACAACCACTACGCGAATCTAATTTACCGCAATAACCACAACTACATTCGCCTCCACA 4010      4020      4030      4040      4050      4060      4070      4080
GGAGACAAATGGTGTAAAAGACTCTAACAAAATAGCAAATTTCGTCAAAAATGCTAAGAAATAGGTTATTACTGAGTAGT
CCTCTGTTTACCACATTTTCTGAGATTGTTTTATCGTTTAAAGCAGTTTTTACGATTCTTTATCCAATAATGACTCATCA 4090      4100      4110      4120      4130      4140      4150      4160
ATTTATTTAAGTATTGTTTGTGCACTTGCCTGCAGGCCTTTTGAAAAGCAAGCATAAAAGATCTAAACATAAAATCTGTA
TAAATAAATTCATAACAAACACGTGAACGGACGTCCGGAAAACTTTTCGTTCGTATTTTCTAGATTTGTATTTAGACAT 4170      4180      4190      4200      4210      4220      4230      4240
AAATAACAAGATGTAAAGATAATGCTAAATCATTTGGCTTTTTGATTGATTGTACAGGAAAATATACATCGCAGGGGGTT
TTTATTGTTCTACATTTCTATTACGATTTAGTAAACCGAAAAACTAACTAACATGTCCTTTTATATGTAGCGTCCCCCAA 4250      4260      4270      4280      4290      4300      4310      4320
GACTTTTACCATTTCACCGCAATGGAATCAAACTTGTTGAAGAGAATGTTCACAGGCGCATACGCTACAATGACCCGATT
CTGAAAATGGTAAAGTGGCGTTACCTTAGTTTGAACAACTTCTCTTACAAGTGTCCGCGTATGCGATGTTACTGGGCTAA 4330      4340      4350      4360      4370      4380      4390      4400
CTTGCTAGCCTTTTCTCGGTCTTGCAAACAACCGCCGGCAGCTTAGTATATAAATACACATGTACATACCTCTCTCCGTA
GAACGATCGGAAAAGAGCCAGAACGTTTGTTGGCGGCCGTCGAATCATATATTTATGTGTACATGTATGGAGAGAGGCAT 4410      4420      4430      4440      4450      4460      4470      4480
TCCTCGTAATCATTTTCTTGTATTTATCGTCTTTTCGCTGTAAAAACTTTATCACTTATCTCAAATACACTTATAACCGC
AGGAGCATTAGTAAAAGAACATAAATAGCAGAAAAGCGACATTTTTGAAATAGTGAATAGAGTTTATGTGAATATTGGCG
```

FIG. 4D

```
      4490      4500      4510      4520      4530      4540      4550      4560
TTTTACTATTATCTTCTACGCTGACAGTAATATCAAACAGTGACACATATTAAACACACAGTGGTTTCTTTGCATAAACA
AAAATGATAATAGAAGATGCGACTGTCATTATAGTTTGTCACTGTGTATAATTTGTGTGTCACCAAAGAAACGTATTTGT 4570      4580      4590      4600      4610      4620      4630      4640
CCATGAGCCTCAAGTCGTCAAGTAAAGATTTCGTGTTCATGCAGATAGATAACAATCTATATGTTGATAATTAGCGTTGC
GGTACTCGGAGTTCAGCAGTTCATTTCTAAAGCACAAGTACGTCTATCTATTGTTAGATATACAACTATTAATCGCAACG 4650      4660      4670      4680      4690      4700      4710      4720
CTCATCAATGCGAGATCCGTTTAACCGGACCCTAGTGCACTTACCCGACGTTCGGTCCACTGTGTGCCGAACATGCTCCT
GAGTAGTTACGCTCTAGGCAAATTGGCCTGGGATCACGTGAATGGGCTGCAAGCCAGGTGACACACGGCTTGTACGAGGA 4730      4740      4750      4760      4770      4780      4790      4800
TCACTATTTTAACATGTGCGTAATCATGGTCATAGCTGTTTCCTGTGTGAAATTGTTATCCGCTCACAATTCCACACAAC
AGTGATAAAATTGTACACGCATTAGTACCAGTATCGACAAAGGACACACTTTAACAATAGGCGAGTGTTAAGGTGTGTTG 4810      4820      4830      4840      4850      4860      4870      4880
ATACGAGCCGGAAGCATAAAGTGTAAAGCCTGGGGTGCCTAATGAGTGAGCTAACTCACATTAATTGCGTTGCGCTCACT
TATGCTCGGCCTTCGTATTTCACATTTCGGACCCCACGGATTACTCACTCGATTGAGTGTAATTAACGCAACGCGAGTGA 4890      4900      4910      4920      4930      4940      4950      4960
GCCCGCTTTCCAGTCGGGAAACCTGTCGTGCCAGCTGCATTAATGAATCGGCCAACGCGCGGGGAGAGGCGGTTTGCGTA
CGGGCGAAAGGTCAGCCCTTTGGACAGCACGGTCGACGTAATTACTTAGCCGGTTGCGCGCCCCTCTCCGCCAAACGCAT 4970      4980      4990      5000      5010      5020      5030      5040
TTGGGCGCTCTTCCGCTTCCTCGCTCACTGACTCGCTGCGCTCGGTCGTTCGGCTGCGGCGAGCGGTATCAGCTCACTCA
AACCCGCGAGAAGGCGAAGGAGCGAGTGACTGAGCGACGCGAGCCAGCAAGCCGACGCCGCTCGCCATAGTCGAGTGAGT 5050      5060      5070      5080      5090      5100      5110      5120
AAGGCGGTAATACGGTTATCCACAGAATCAGGGGATAACGCAGGAAAGAACATGTGAGCAAAAGGCCAGCAAAAGGCCAG
TTCCGCCATTATGCCAATAGGTGTCTTAGTCCCCTATTGCGTCCTTTCTTGTACACTCGTTTTCCGGTCGTTTTCCGGTC 5130      5140      5150      5160      5170      5180      5190      5200
GAACCGTAAAAAGGCCGCGTTGCTGGCGTTTTTCCATAGGCTCCGCCCCCCTGACGAGCATCACAAAAATCGACGCTCAA
CTTGGCATTTTTCCGGCGCAACGACCGCAAAAAGGTATCCGAGGCGGGGGGACTGCTCGTAGTGTTTTTAGCTGCGAGTT 5210      5220      5230      5240      5250      5260      5270      5280
GTCAGAGGTGGCGAAACCCGACAGGACTATAAAGATACCAGGCGTTTCCCCCTGGAAGCTCCCTCGTGCGCTCTCCTGTT
CAGTCTCCACCGCTTTGGGCTGTCCTGATATTTCTATGGTCCGCAAAGGGGGACCTTCGAGGGAGCACGCGAGAGGACAA 5290      5300      5310      5320      5330      5340      5350      5360
CCGACCCTGCCGCTTACCGGATACCTGTCCGCCTTTCTCCCTTCGGGAAGCGTGGCGCTTTCTCAATGCTCACGCTGTAG
GGCTGGGACGGCGAATGGCCTATGGACAGGCGGAAAGAGGGAAGCCCTTCGCACCGCGAAAGAGTTACGAGTGCGACATC 5370      5380      5390      5400      5410      5420      5430      5440
GTATCTCAGTTCGGTGTAGGTCGTTCGCTCCAAGCTGGGCTGTGTGCACGAACCCCCCGTTCAGCCCGACCGCTGCGCCT
CATAGAGTCAAGCCACATCCAGCAAGCGAGGTTCGACCCGACACACGTGCTTGGGGGCAAGTCGGGCTGGCGACGCGGA 5450      5460      5470      5480      5490      5500      5510      5520
TATCCGGTAACTATCGTCTTGAGTCCAACCCGGTAAGACACGACTTATCGCCACTGGCAGCAGCCACTGGTAACAGGATT
ATAGGCCATTGATAGCAGAACTCAGGTTGGGCCATTCTGTGCTGAATAGCGGTGACCGTCGTCGGTGACCATTGTCCTAA 5530      5540      5550      5560      5570      5580      5590      5600
AGCAGAGCGAGGTATGTAGGCGGTGCTACAGAGTTCTTGAAGTGGTGGCCTAACTACGGCTACACTAGAAGGACAGTATT
TCGTCTCGCTCCATACATCCGCCACGATGTCTCAAGAACTTCACCACCGGATTGATGCCGATGTGATCTTCCTGTCATAA
```

FIG. 4E

```
         5610      5620      5630      5640      5650      5660      5670      5680
TGGTATCTGCGCTCTGCTGAAGCCAGTTACCTTCGGAAAAAGAGTTGGTAGCTCTTGATCCGGCAAACAAACCACCGCTG
ACCATAGACGCGAGACGACTTCGGTCAATGGAAGCCTTTTTCTCAACCATCGAGAACTAGGCCGTTTGTTTGGTGGCGAC 5690      5700      5710      5720      5730      5740      5750      5760
GTAGCGGTGGTTTTTTTGTTTGCAAGCAGCAGATTACGCGCAGAAAAAAAGGATCTCAAGAAGATCCTTTGATCTTTTCT
CATCGCCACCAAAAAAACAAACGTTCGTCGTCTAATGCGCGTCTTTTTTTCCTAGAGTTCTTCTAGGAAACTAGAAAAGA 5770      5780      5790      5800      5810      5820      5830      5840
ACGGGGTCTGACGCTCAGTGGAACGAAAACTCACGTTAAGGGATTTTGGTCATGAGATTATCAAAAAGGATCTTCACCTA
TGCCCCAGACTGCGAGTCACCTTGCTTTTGAGTGCAATTCCCTAAAACCAGTACTCTAATAGTTTTTCCTAGAAGTGGAT 5850      5860      5870      5880      5890      5900      5910      5920
GATCCTTTTAAATTAAAAATGAAGTTTTAAATCAATCTAAAGTATATATGAGTAAACTTGGTCTGACAGTTACCAATGCT
CTAGGAAAATTTAATTTTTACTTCAAAATTTAGTTAGATTTCATATATACTCATTTGAACCAGACTGTCAATGGTTACGA 5930      5940      5950      5960      5970      5980      5990      6000
TAATCAGTGAGGCACCTATCTCAGCGATCTGTCTATTTCGTTCATCCATAGTTGCCTGACTCCCCGTCGTGTAGATAACT
ATTAGTCACTCCGTGGATAGAGTCGCTAGACAGATAAAGCAAGTAGGTATCAACGGACTGAGGGGCAGCACATCTATTGA 6010      6020      6030      6040      6050      6060      6070      6080
ACGATACGGGAGGGCTTACCATCTGGCCCCAGTGCTGCAATGATACCGCGAGACCCACGCTCACCGGCTCCAGATTTATC
TGCTATGCCCTCCCGAATGGTAGACCGGGGTCACGACGTTACTATGGCGCTCTGGGTGCGAGTGGCCGAGGTCTAAATAG 6090      6100      6110      6120      6130      6140      6150      6160
AGCAATAAACCAGCCAGCCGGAAGGGCCGAGCGCAGAAGTGGTCCTGCAACTTTATCCGCCTCCATCCAGTCTATTAATT
TCGTTATTTGGTCGGTCGGCCTTCCCGGCTCGCGTCTTCACCAGGACGTTGAAATAGGCGGAGGTAGGTCAGATAATTAA 6170      6180      6190      6200      6210      6220      6230      6240
GTTGCCGGGAAGCTAGAGTAAGTAGTTCGCCAGTTAATAGTTTGCGCAACGTTGTTGCCATTGCTACAGGCATCGTGGTG
CAACGGCCCTTCGATCTCATTCATCAAGCGGTCAATTATCAAACGCGTTGCAACAACGGTAACGATGTCCGTAGCACCAC 6250      6260      6270      6280      6290      6300      6310      6320
TCACGCTCGTCGTTTGGTATGGCTTCATTCAGCTCCGGTTCCCAACGATCAAGGCGAGTTACATGATCCCCCATGTTGTG
AGTGCGAGCAGCAAACCATACCGAAGTAAGTCGAGGCCAAGGGTTGCTAGTTCCGCTCAATGTACTAGGGGGTACAACAC 6330      6340      6350      6360      6370      6380      6390      6400
CAAAAAAGCGGTTAGCTCCTTCGGTCCTCCGATCGTTGTCAGAAGTAAGTTGGCCGCAGTGTTATCACTCATGGTTATGG
GTTTTTTCGCCAATCGAGGAAGCCAGGAGGCTAGCAACAGTCTTCATTCAACCGGCGTCACAATAGTGAGTACCAATACC 6410      6420      6430      6440      6450      6460      6470      6480
CAGCACTGCATAATTCTCTTACTGTCATGCCATCCGTAAGATGCTTTTCTGTGACTGGTGAGTACTCAACCAAGTCATTC
GTCGTGACGTATTAAGAGAATGACAGTACGGTAGGCATTCTACGAAAAGACACTGACCACTCATGAGTTGGTTCAGTAAG 6490      6500      6510      6520      6530      6540      6550      6560
TGAGAATAGTGTATGCGGCGACCGAGTTGCTCTTGCCCGGCGTCAATACGGGATAATACCGCGCCACATAGCAGAACTTT
ACTCTTATCACATACGCCGCTGGCTCAACGAGAACGGGCCGCAGTTATGCCCTATTATGGCGCGGTGTATCGTCTTGAAA 6570      6580      6590      6600      6610      6620      6630      6640
AAAAGTGCTCATCATTGGAAAACGTTCTTCGGGGCGAAAACTCTCAAGGATCTTACCGCTGTTGAGATCCAGTTCGATGT
TTTTCACGAGTAGTAACCTTTTGCAAGAAGCCCCGCTTTTGAGAGTTCCTAGAATGGCGACAACTCTAGGTCAAGCTACA 6650      6660      6670      6680      6690      6700      6710      6720
AACCCACTCGTGCACCCAACTGATCTTCAGCATCTTTTACTTTCACCAGCGTTTCTGGGTGAGCAAAAACAGGAAGGCAA
TTGGGTGAGCACGTGGGTTGACTAGAAGTCGTAGAAAATGAAAGTGGTCGCAAAGACCCACTCGTTTTTGTCCTTCCGTT
```

FIG. 4F

```
        6730      6740      6750      6760      6770      6780      6790      6800
AATGCCGCAAAAAAGGGAATAAGGGCGACACGGAAATGTTGAATACTCATACTCTTCCTTTTTCAATATTATTGAAGCAT
TTACGGCGTTTTTTCCCTTATTCCCGCTGTGCCTTTACAACTTATGAGTATGAGAAGGAAAAAGTTATAATAACTTCGTA 6810      6820      6830      6840      6850      6860      6870      6880
TTATCAGGGTTATTGTCTCATGAGCGGATACATATTTGAATGTATTTAGAAAAATAAACAAATAGGGGTTCCGCGCACAT
AATAGTCCCAATAACAGAGTACTCGCCTATGTATAAACTTACATAAATCTTTTTATTTGTTTATCCCCAAGGCGCGTGTA 6890      6900      6910      6920      6930      6940      6950      6960
TTCCCCGAAAAGTGCCACCTGACGTCTAAGAAACCATTATTATCATGACATTAACCTATAAAAATAGGCGTATCACGAGG
AAGGGGCTTTTCACGGTGGACTGCAGATTCTTTGGTAATAATAGTACTGTAATTGGATATTTTTATCCGCATAGTGCTCC 6970      6980      6990      7000      7010      7020      7030      7040
CCCTTTCGTCTTCAAGAA
GGGAAAGCAGAAGTTCTT
```

FIG. 4G

```
           10         20         30         40         50
     GGTCAATACA AATCCATCAT GAAGACCTTT CTCATCCTTG CCCTCGTGGC
     CCAGTTATGT TTAGGTAGTA CTTCTGGAAA GAGTAGGAAC GGGAGCACCG 60         70         80         90        100
     GACCACCGCC ACAACTGCAG TTAGAGTTCC AGTGCCACAA TTGCAGCCAA
     CTGGTGGCGG TGTTGACGTC AATCTCAAGG TCACGGTGTT AACGTCGGTT 110        120        130        140        150
     AAAATCCATC TCAGCAACAG CCACAAGAGC AAGTTCCATT GGTACAACAA
     TTTTAGGTAG AGTCGTTGTC GGTGTTCTCG TTCAAGGTAA CCATGTTGTT 160        170        180        190        200
     CAACAATTTC CAGGGCAGCA ACAACAATTT CCACCACAAC AGCCATATCC
     GTTGTTAAAG GTCCCGTCGT TGTTGTTAAA GGTGGTGTTG TCGGTATAGG 210        220        230        240        250
     GCAGCCGCAA CCATTTCCAT CACAACAACC ATATCTGCAG CTGCAACCAT
     CGTCGGCGTT GGTAAAGGTA GTGTTGTTGG TATAGACGTC GACGTTGGTA 260        270        280        290        300
     TTCCGCAGCC GCAACCATTT CTGCCACAAC TACCATATCC GCAGCCGCAA
     AAGGCGTCGG CGTTGGTAAA GACGGTGTTG ATGGTATAGG CGTCGGCGTT 310        320        330        340        350
     TCATTTCCAC CACAACAACC ATATCCACAA CAGCGACCAA AGTATCTACA
     AGTAAAGGTG GTGTTGTTGG TATAGGTGTT GTCGCTGGTT TCATAGATGT 360        370        380        390        400
     ACCACAACAA CCAATTTCGC AGCAACAAGC ACAACAACAA CAACAACAAC
     TGGTGTTGTT GGTTAAAGCG TCGTTGTTCG TGTTGTTGTT GTTGTTGTTG 410        420        430        440        450
     AACAACAACA ACAACAACAA CAACAACAAC AAATCCTTCA ACAAATTTTG
     TTGTTGTTGT TGTTGTTGTT GTTGTTGTTG TTTAGGAAGT TGTTTAAAAC 460        470        480        490        500
     CAACAACAAC TGATTCCATG CAGGGATGTT GTCTTGCAAC AACACAACAT
     GTTGTTGTTG ACTAAGGTAC GTCCCTACAA CAGAACGTTG TTGTGTTGTA 510        520        530        540        550
     AGCGCATGCA AGCTCACAAG TTTTGCAACA AAGTACTTAC CAGCTATTGC
     TCGCGTACGT TCGAGTGTTC AAAACGTTGT TTCATGAATG GTCGATAACG 560        570        580        590        600
     AACAATTGTG TTGTCAACAA CTGTTGCAGA TCCCTGAGCA GTCGAGGTGC
     TTGTTAACAC AACAGTTGTT GACAACGTCT AGGGACTCGT CAGCTCCACG 610        620        630        640        650
     CAAGCCATCC ATAATGTTGT TCATGCTATT ATTATGCATC AACAAGAACA
     GTTCGGTAGG TATTACAACA AGTACGATAA TAATACGTAG TTGTTCTTGT
```

FIG. 5A

```
       660        670        680        690        700
ACAACAACAG TTGCAACAAC AACAACAACA GCAACTGCAA CAACAACAAC
TGTTGTTGTC AACGTTGTTG TTGTTGTTGT CGTTGACGTT GTTGTTGTTG 710        720        730        740        750
AACAACAACA ACAACAACAA CAACCGTCAA GCCAGGTCTC CTTCCAACAG
TTGTTGTTGT TGTTGTTGTT GTTGGCAGTT CGGTCCAGAG GAAGGTTGTC 760        770        780        790        800
CCTCAGCAGC AATATCCATC AAGCCAGGTC TCCTTCCAGC CATCTCAGCT
GGAGTCGTCG TTATAGGTAG TTCGGTCCAG AGGAAGGTCG GTAGAGTCGA 810        820        830        840        850
AAACCCACAA GCTCAGGGCT CCGTCCAACC TCAACAACTG CCCCAGTTCG
TTTGGGTGTT CGAGTCCCGA GGCAGGTTGG AGTTGTTGAC GGGGTCAAGC 860        870        880        890        900
CGGAAATAAG GAACCTAGCG CTACAGACGC TACCTGCAAT GTGCAATGTC
GCCTTTATTC CTTGGATCGC GATGTCTGCG ATGGACGTTA CACGTTACAG 910        920        930        940        950
TACATCCCTC CACATTGCTC GACCACCATT GCGCCATTTG GCATCTTTGG
ATGTAGGGAG GTGTAACGAG CTGGTGGTAA CGCGGTAAAC CGTAGAAACC 960        970        980        990       1000
TACCAACTGA GAAGAGAAGA ACTCTAGTAC TAGATATATG AAACACCGTT
ATGGTTGACT CTTCTCTTCT TGAGATCATG ATCTATATAC TTTGTGGCAA

1010
TTCTTAGTCC ATGATT
AAGAATCAGG TACTAA
```

FIG. 5B

YEAST STRAINS GENETICALLY ENGINEERED TO PRODUCE WHEAT GLUTEN PROTEINS

BACKGROUND OF THE INVENTION

1 Field of the Invention

This invention relates to the use of recombinant DNA technology to produce yeast strains that will produce wheat gluten proteins and to plasmids which include genes coding for wheat gluten proteins.

2. Description of the Art

Recently developed recombinant deoxyribonucleic acid (DNA) techniques have made it possible to utilize microorganisms for synthesis of commercially useful proteins and peptides which are normally made by other organisms. Briefly, the procedure involves: (1) isolation and purification of the specific gene or gene segment containing the genetically coded information for the amino acid sequence of the desired protein, (2) recombination of the isolated gene segment with an appropriate transfer vector, and (3) transfer of the vector to the appropriate microorganism and selection of a strain of microorganism containing the desired information.

Examples of foreign genes expresssed in yeast include the wheat α-amylase gene (Rothstein et al., *Nature* 308: 662–665 (1984)), human epidermal growth factor (Brake et al., *Proc. Natl. Acad. Sci. U.S.A.* 81: 4642–4646 (1984)), chicken egg white lysozyme (Oberto and Davidson, *Gene* 40: 57–65 (1985)), and *Torpedo californica* acetylcholine receptor α subunit (Fujita et al., *Science* 231: 1284–1287 (1986)). A fragment of the maize seed storage protein, zein, has also been produced in yeast (Coraggio et al., *EMBO J.* 5: 459–465 (1986)).

There is no report in the prior art of expression of a wheat gluten gene in lower eukaryotes, for example yeast. Wheat gluten proteins consist of gliadin and glutenin proteins. The gliadins are monomeric proteins of 30,000 to 78,000 molecular weight; they comprise a multigene family and have been historically assigned to α, β, γ, and w classes based on electrophoretic mobility. They constitute a major fraction of the seed storage proteins of hexaploid wheat grain and are important dietary proteins and determinants of dough and bread baking quality. In addition, gliadins, or peptides derived from them during digestion, initiate damage to the absorptive epithelium of the small intestine to produce symptoms of celiac disease in susceptible individuals.

While production of wheat gluten proteins by yeast strains would be of considerable value for production of pure proteins for use in diagnosis and treatment of celiac disease, for testing theories of dough formation, or for supplementation of baking formulations, heretofore no yeast having this capability has been made. Problems inherent in the expression of a wheat gluten gene in yeast include the following: (1) extreme differences in amino acid codon preference between gluten protein mRNAs and abundant yeast protein mRNAs make predictions regarding the compatibility of gluten mRNAs with the yeast protein synthesis system impossible; (2) lack of prior knowledge regarding the stability of wheat gluten protein mRNAs in yeast make predictions of the actual synthesis of complete gluten protein molecules in yeast impossible; (3) lack of prior knowledge of the toxicity, if any, of wheat gluten proteins to yeast make predictions of the maintenance of viable wheat gluten protein-producing yeast strains impossible; and (4) lack of knowledge of the compatibility of the yeast α-gliadin precursor with the protein processing systems of yeast make it impossible to predict whether the signal peptide would be cleaved from the α-gliadin precursor to produce the mature protein.

SUMMARY OF THE INVENTION

A strain of yeast *Saccharomyces cerevisiae* has been developed which, when grown under defined culture conditions, will produce a protein indistinguishable from the wheat gluten protein, α-gliadin, by criteria of molecular size and immunochemical reactivity. This new yeast strain was developed by introduction of a specially constructed autonomously replicating extrachromasomal genetic element, gluten plasmid pAY31, into a non-gluten protein producing yeast strain and differs from its parent by the genetic information contained in the plasmid.

Gluten plasmid pAY31 is a circular DNA molecule, constructed by enzymic fusion of the following elements: (1) the *Escherichia coli* plasmid pUC8 wherein the EcoRI site has been removed; (2) the autonomously replicating yeast sequence ARS1; (3) the yeast URA3 gene; (4) a modified yeast iso-1-cytochrome c (CYC1) gene retaining the promoter region and transcription termination sequence, and wherein the protein coding sequences have been deleted and replaced with a synthetic EcoRI restriction site, the site at which the wheat gluten gene is cloned; and (5) a gene fragment of wheat α-gliadin α1Y consisting of the amino acid region, translation initiation and termination sequences, and short flanking nucleotide sequences, but excluding transcription initiation and termination sequences.

Strains of yeast capable of synthesizing other wheat gluten proteins are prepared by utilizing the gene fragment for the desired protein, instead of that for α-gliadin, as element (5) of the gluten plasmid constructed as described above. For example, a strain of yeast capable of producing β-gliadin protein is prepared by inserting into the plasmid a β-gliadin gene segment having the amino acid coding region, translation initiation, and termination sequences for β-gliadin instead of those for α-gliadin. Using this procedure, other yeast strains can be prepared which are capable of synthesizing any wheat gluten protein for which a gene is available.

Yeast strains that produce proteins of non-yeast origin have been previously developed, but the above described-strain is the first one known capable of producing a wheat gluten protein or a complete cereal seed storage protein of any kind. This invention is new and unexpected in that: (1) the amino acid codon contents of wheat gluten genes are sufficiently different from the codon useage patterns of yeast to render the likelihood of wheat gluten production in yeast uncertain; (2) it was not predictable that the required mRNA would be sufficiently stable in the new yeast strain to allow production of the wheat gluten protein; (3) the potential toxicity of the wheat gluten protein to yeast was unknown; and (4) the characteristics of the yeast protein processing systems were unknown so that it was not predictable that the signal protein would be appropriately cleaved from the α-gliadin precursor to produce the mature protein.

The invention is applicable to the fields of food technology and medicine. The gluten proteins of the wheat seed are essential determinants of the behavior of wheat flour in formation of doughs and batters used to prepare bread, pasta, cake, and cookie products; and different proteins have different effects in this regard. Supplementation of doughs and batters with specific proteins produced by this invention allows modification of production processes and reduction of unit costs. Such supplementation may also yield bread, cake, pasta, and cookie products with greater consumer acceptability or greater nutritional value.

This invention can also be used to produce pure proteins for use in the diagnosis and treatment of illness in humans caused by wheat gluten proteins and for testing theories of dough formation.

In accordance with this discovery it is an object of the invention to provide new strains of yeast capable of synthesizing wheat gluten proteins.

Another object of this invention is to provide wheat gluten plasmids for insertion into yeast strains for production of wheat proteins.

It is a further object to provide a method for producing yeast strains capable of synthesizing wheat gluten proteins.

Another object of this invention is the provision of pure wheat gluten proteins for use in foods or medicine.

Other objects and advantages of the invention will become readily apparent from the ensuing description.

BRIEF DESCRIPTION OF THE DRAWINGS

FIGS. 4A–4G show the nucleotide sequence of plasmid pAY31.

FIGS. 5A–5B show the nucleotide sequence of the α-gliadin gene fragment used to construct pAY32.

DETAILED DESCRIPTION OF THE INVENTION

Figure 1:
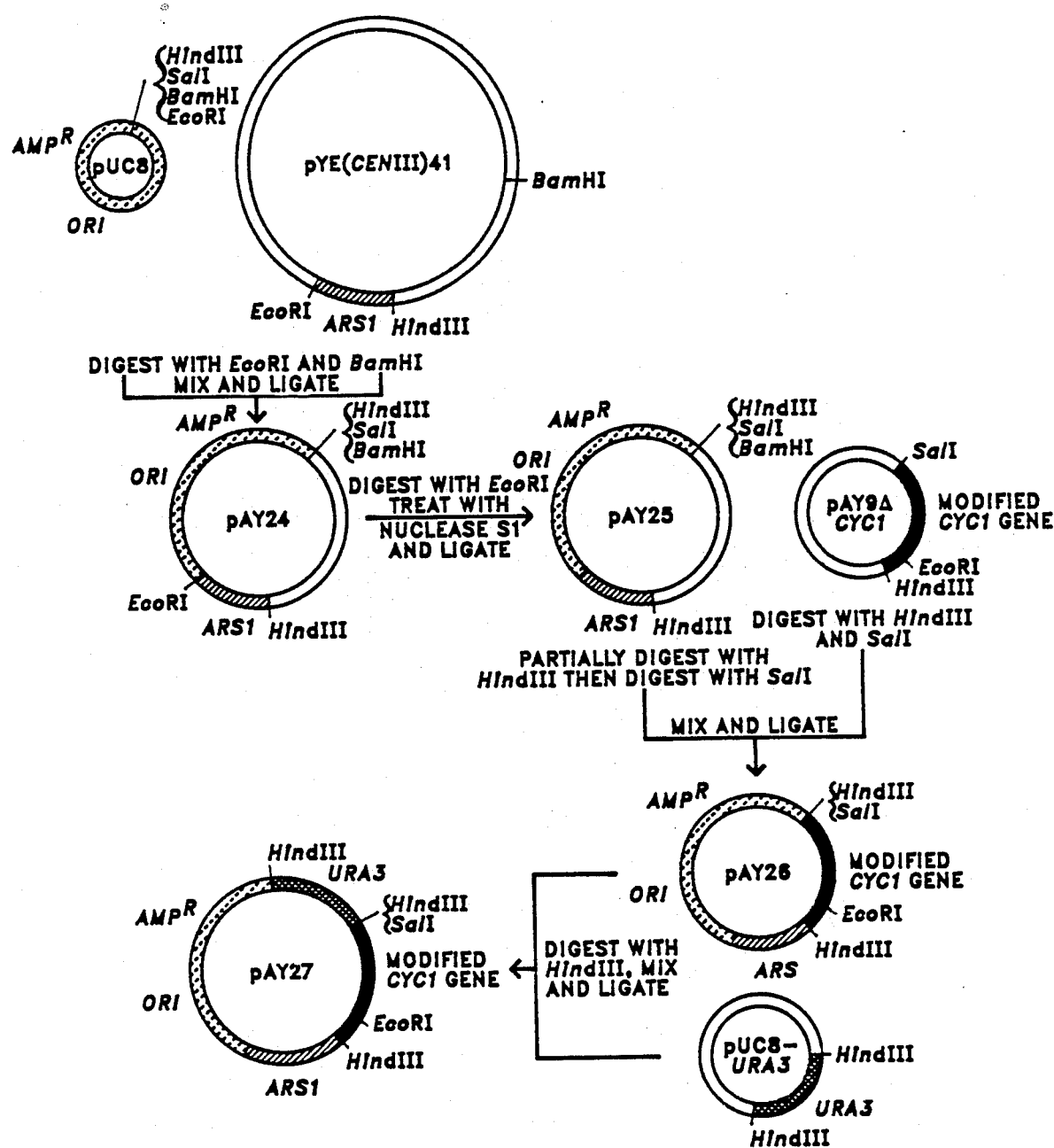
FIG. 1 is a schematic diagram of the construction of expression vector pAY27.

The invention comprises yeast strains capable of producing wheat gluten proteins and methods of preparing the same. The new strains are prepared by introducing into a parent yeast strain a wheat gluten recombinant plasmid which contains as its major elements: (1) a modification of the plasmid pUC8 which carries all the genes necessary for replication of the recombinant plasmid in $E.$ $coli$ and carries the β-lactamase gene (amp$^r$) which serves as a selectable marker in bacteria, but from which the restriction endonuclease EcoRI recognition/cleavage site has been removed; (2) the yeast sequence ARS1, to allow autonomous replication of plasmid in yeast; (3) the yeast URA3 gene, to confer uracil prototrophy and maintain positive selection pressure for cells containing the plasmid and which serves as a selectable marker for transformed yeast cells; (4) a modified yeast CYC1 gene having the upstream activation sequences and promoter elements of the gene, to facilitate regulated transcription of the inserted gluten gene segment, and the transcription termination control element of the CYC1 gene, to facilitate proper termination of transcription of the inserted gene segment and production of functional messenger RNA, but lacking the protein coding sequences which have been deleted and replaced with a synthetic EcoRI restriction site, the site at which the wheat gluten gene is cloned; and (5) the inserted wheat gluten protein gene segment, consisting of the amino acid coding region, translation initiation and termination sequences, and short flanking nucleotide sequences, but excluding transcription initiation and termination sequences.

For construction of a plasmid which provides for production of α-gliadin in yeast, a genomic wheat α-gliadin gene fragment consisting of the entire 858 base pairs (bp) of protein coding sequences, 18 bp of 5' leader sequences, and 54 bp of 3' non-coding sequences was inserted into the EcoRI expression site of the modified CYC1 gene. The α-gliadin plasmid was next transformed into a ura3- yeast strain (having a mutation in the URA3 gene). Selection of transformed yeast strains was carried out by growing the strains on uracil omission medium.

As described below when plasmid pAY31, which includes the α-gliadin gene segment, was transformed into $S.$ $cerevisiae,$ the transformed strain produced an abundant CYC1-α-gliadin transcript of approximately 1050 bases, synthesized in the transformed yeast under the control of the CYC1 regulatory region. The transcript terminated within the α-gliadin 3' non-coding sequences, near a nucleotide sequence similar to the yeast transcription termination consensus sequence. The protein produced by the transformed yeast was indistinguishable from α-gliadin by criteria of molecular size and immunochemical reactivity. α-gliadin detected in total protein extracts from transformed cells accounted for approximately 0.1% of the total cellular protein. The size of α-gliadin synthesized by the transformed yeast is the same as mature α-gliadin in wheat indicating that the primary translation product undergoes a post-translational modification in yeast similar to that which it undergoes in wheat, i.e., the α-gliadin precursor signal peptide is cleaved.

Production of transformed yeast strains capable of producing other wheat gluten proteins, e.g., β-gliadin, γ-gliadin, or glutenin, are constructed by inserting a segment of the desired wheat gluten protein gene, the segment having the amino acid coding region, translation initiation and termination sequences, and short flanking nucleotide sequences, but excluding transcription initiation and termination sequences as element (5) of the gluten plasmid described above. For example, a yeast strain capable of synthesizing β-gliadin of 33.9 kilodaltons molecular weight is prepared by incorporating a segment of the β-gliadin gene CY10, described below, as element (5), followed by transformation of the parent yeast strain.

To facilitate expression of a wheat gene in yeast, an expression vector was prepared by application of several techniques, including (1) digestive cleavage of DNA at specific nucleotide sequences (restriction endonuclease cleavage); (2) sequential enzymic removal of nucleotides from the ends of the DNA molecules (exonuclease digestion); (3) covalent enzymic joining of linear DNA molecules (ligation); and (4) plasmid or bacteriophage-induced transformation of bacteria (cloning). Descriptions of these techniques can be found in the publications by Maniatis et al., *Molecular Cloning: A Laboratory Manual,* Cold Spring Harbor Press (1982), and Wu et al. (Eds.) *Methods in Enzymology,* Vol. 100, Sections I and IV (1983). Next, a wheat gluten plasmid was constructed by subcloning a portion of a genomic wheat α-gliadin gene into the CYC1-directed expression site of the expression vector to obtain a gliadin recombinant plasmid. Finally, a strain of $S.$ $cerevisiae$ was transformed with the wheat gluten plasmid.

EXAMPLES

The present invention is more fully described by, but not limited to, the following examples.

EXAMPLE 1

Construction of the Expression Vector pAY27

The expression vector pAY27 was constructed to express foreign genes in the yeast *S. cerevisiae*. The vector contains the origin of replication and the β-lactamase gene from the *E. coli* plasmid pUC8, the yeast URA3 gene, the yeast origin of replication (ARS1), and the modified yeast CYC1 gene from which the protein coding sequences have been deleted. The modified CYC1 gene contains a single EcoRI restriction site into which the wheat gluten protein gene is cloned. pAY27 was constructed following the scheme illustrated in FIG. 1.

A. Subcloning of the *S. cerevisiae* ARS1 sequence into pUC8.

The plasmid pYE(CENIII)41 (Clarke and Carbon, *Nature* 287: 504–509 (1980) was digested with the restriction endonucleases BamHI and EcoRI and the DNA was electrophoresed on a preparative agarose gel. The 2.8 kbp fragment containing the ARS1 sequence was recovered and ligated into BamHI-EcoRI-digested pUC8. The ligation mixture was transformed into *E. coli*, plated to obtain individual colonies, and transformants analyzed by cracking gels to determine which contained inserts within the plasmid. One plasmid, designated as pAY24, was analyzed by restriction endonuclease analysis and found to have band patterns expected for the ARS1 sequence cloned into pUC8. This plasmid is 5.52 kbp in size.

In order to have only a single EcoRI restriction site (CYC1-directed expression site) in the final vector, the EcoRI site at the junction of the ARS1 and pUC8 sequences was removed from pAY24 by digestion of pAY24 with EcoRI, treatment of the EcoRI complementary ends with nuclease S1, and recircularization of the plasmids by blunt-end ligation. This plasmid was designated pAY25. Restriction endonuclease analysis of pAY25 indicated that the EcoRI restriction site was removed from the plasmid and that no other changes had occurred in the plasmid as a result of the nuclease S1 digestion. The size of the plasmid is 5.52 kbp.

B. Construction of the CYC1-directed Expression Site

The construction of the CYC1-directed expression site was carried out in such a way that all of the protein coding sequences were deleted but the transcriptional control sequences were left intact. In the initial stage of construction of the cloning and expression site, the EcoRI restriction site present in plasmid pUC8 (Viera and Messing, *Gene* 19: 259–268 (1982)) was removed by digestion with EcoRI, removal of the complementary ends with nuclease S1 digestion, and recircularization of the plasmid by blunt-end ligation. The recircularized plasmids were transformed into *E. coli* JM83 (ara, Δlac-pro, strA, thi, φ80dlacZΔM15) (Viera and Messing, supra) according to the method of Hanahan, *J. Mol. Biol.* 166: 557–580 (1983), and transformants were analyzed to demonstrate the loss of the EcoRI restriction site. One plasmid, designated as pAY13, was selected for further use in construction of the cloning and expression site.

The *S. cervisiae* CYC1 gene was subcloned into pAY13 by digestion of plasmid pAB16 (Stiles et al., *Cell* 25: 277–284 (1983)) with HindIII and SalI. The 1.7 kilobase pairs (kbp) HindIII-SalI CYC1 fragment was removed from pAB16 and ligated into pAY13 that had been digested with HindIII and SalI. This plasmid was designated as pAY9. Restriction endonuclease analysis and analysis with XhoI confirmed the presence of the CYC1 gene. Plasmid pAY9 consists of the CYC1 sequences between the HindIII site at nucleotide 1 and the SalI site at 1.68 kbp and the pUC8 sequences between the SalI site at 1.68 kbp and the HindIII at 4.38 kbp. The distance of the restriction sites are measured from the HindIII restriction site at the junction of the CYC1 and pUC8 sequences.

Next, the protein coding sequences of the CYC1 gene were deleted. First, pAY9 was digested with EcoRI to linearize the plasmid at the unique EcoRI restriction site located within the third and fourth codons of the CYC1 protein coding sequences. The linearized plasmid was treated with nuclease Bal-31 at a concentration calculated to delete through the ATG initiation codon with 5 minutes of incubation (0.3 units/ml). Phosphorylated EcoRI synthetic linkers were blunt-end ligated onto the ends of the plasmid, the EcoRI complementary ends were generated within the linker sequences by digestion with EcoRI, and the plasmid was recircularized by ligation.

The remaining coding sequences of the CYC1 gene were then deleted as follows. Digestion with KpnI cut the plasmid DNA at the unique KpnI restriction site located 81 bp 5' of the TAA termination codon. The plasmid DNA was treated with nuclease Bal-31 at an enzyme concentration sufficient to delete through the TAA with 5 minutes of incubation (1 unit/ml). Phosphorylated EcoRI linkers were ligated onto the ends of the plasmids and the DNA was digested with EcoRI. The digestion generated EcoRI complementary ends within the new linker sequences and also cut at the EcoRI linker which had been previously inserted into the plasmid after generation of the first deletion. This resulted in the release of the DNA fragment containing the CYC1 protein coding sequences between the first EcoRI linker and the end point of the second deletion. The plasmid was recircularized by ligation under conditions that did not allow ligation of the protein coding DNA sequence back into the plasmid. This plasmid was designated pAY9ΔCYC1. The size of this plasmid is 4.06 kbp. DNA sequence analysis determined that the first nuclease Bal-31 treatment resulted in the deletion of the ATG initiation codon as well as 11 bp of the 5' non-coding region. The second deletion generated by nuclease Bal-31 digestion resulted in the deletion of the remaining protein coding region as well as 11 bp of the 3' non-coding sequences. This analysis confirmed that the protein coding sequence of the CYC1 gene was removed and replaced by the EcoRI restriction site.

C. Subcloning of the modified CYC1 gene into pAY25 from pAY9-ΔCYC1.

pAY25 was digested with HindIII in the presence of ethidium bromide, conditions that allow only one of the two HindIII sites in this plasmid to be cleaved. After removal of the ethidium bromide by isoamyl alcohol extraction, the DNA was digested with SalI, electrophoresed to separate the DNA fragments, and the 3.5 kbp HindIII-SalI fragment recovered from the gel. pAY9-ΔCYC1 was digested with HindIII and SalI and the DNA was electrophoresed on a preparative agarose gel. The 1.33 kbp band was removed from the gel, pooled with the 3.5 kbp fragment from above and ligated. The DNA was transformed into *E. coli*, and the transformants were picked at random and were analyzed on cracking gels. One plasmid containing an insert was picked, isolated, and analyzed for the proper insert by restriction endonuclease digestion. The resulting band patterns were consistent with the insertion of the modified CYC1 gene into pAY25 between the HindIII site at the border of the ARS1 sequences and the SalI site near nucleotide 1. This plasmid, designated pAY26, is 4.9 kbp in size, and contains the modified CYC1 sequences between the HindIII site and the SalI site, as well as ARS1 sequences and pUC8 sequences.

D. Subcloning of *S. cerevisiae* selectable marker URA3 into pAY26.

The *S. cerevisiae* selectable marker, URA3, (Rose et al., *Gene* 29: 113–124 (1984)) was subcloned into pAY26 to complete construction of the expression vector. The plasmid pUC8-URA3 was digested with HindIII and was eectrophoresed on a preparative agarose gel. The 1.15 kbp fragment containing the URA3 gene was removed and ligated into pAY26 that had been linearized by digestion with HindIII in the presence of ethidium bromide and purified by preparative agarose gel electrophoresis. The DNA was transformed into *E. coli*, and the transformants were analyzed for the presence of the URA3 insert. One plasmid was chosen and analyzed by restriction endonuclease analysis. This plasmid, designated pAY27, is made up of the URA3 gene between the HindIII sites at nucleotide 1 and 1.18 kbp, the modified CYC1 fragment between the SalI site at 1.18 kbp and the HindIII site at 2.51 kbp, the ARS1 sequences between the HindIII site at 2.51 kbp and the EcoRI site that was removed at 3.37 kbp and pUC8 between 3.37 kbp and 6.05 kbp (FIG. 1). All distances of the restriction sites are measured in kbp from the HindIII site located at the junction of pUC8 and the URA3 gene. The plasmid has the β-lactamase gene (amp$^r$) as a selectable marker in *E. coli* and the URA3 gene as a selectable marker in yeast. The plasmid can be grown as an episome in both *E. coli* and yeast as it contains an *E. coli* origin of replication and the ARSI sequence which is presumed to be an origin of replication in yeast. The single EcoRI restriction site of the plasmid is the cloning site of genes that are to be expressed in yeast under control of the CYC1 promoter. The cloning site is flanked by the CYC1 promoter and the catabolite control sequences and by the transcription termination sequences.

pAY27 was tested for its ability to transform ura3- yeast strains to the URA+ phenotype using yeast strain D1113-1OB. Transformed cells were selected by plating on -ura omission medium plates. After incubation for 3 to 5 days, transformed colonies appeared on the plates at the rate of approximately 200 to 400 transformants/ug of vector DNA. pAY27 is maintained in transformed yeast by selecting for uracil prototrophy in yeast containing a mutation in the URA3 gene.

pAY27 contained in *E. coli* is on permanent deposit with the culture collection of the Northern Regional Research Center, Agricultural Research Service, U.S. Department of Agriculture, Peoria, Ill., and has been assigned the accession No. NRRL B-18120.

EXAMPLE 2

Construction of Gliadin Recombinant Plasmid pAY31

Figure 2:
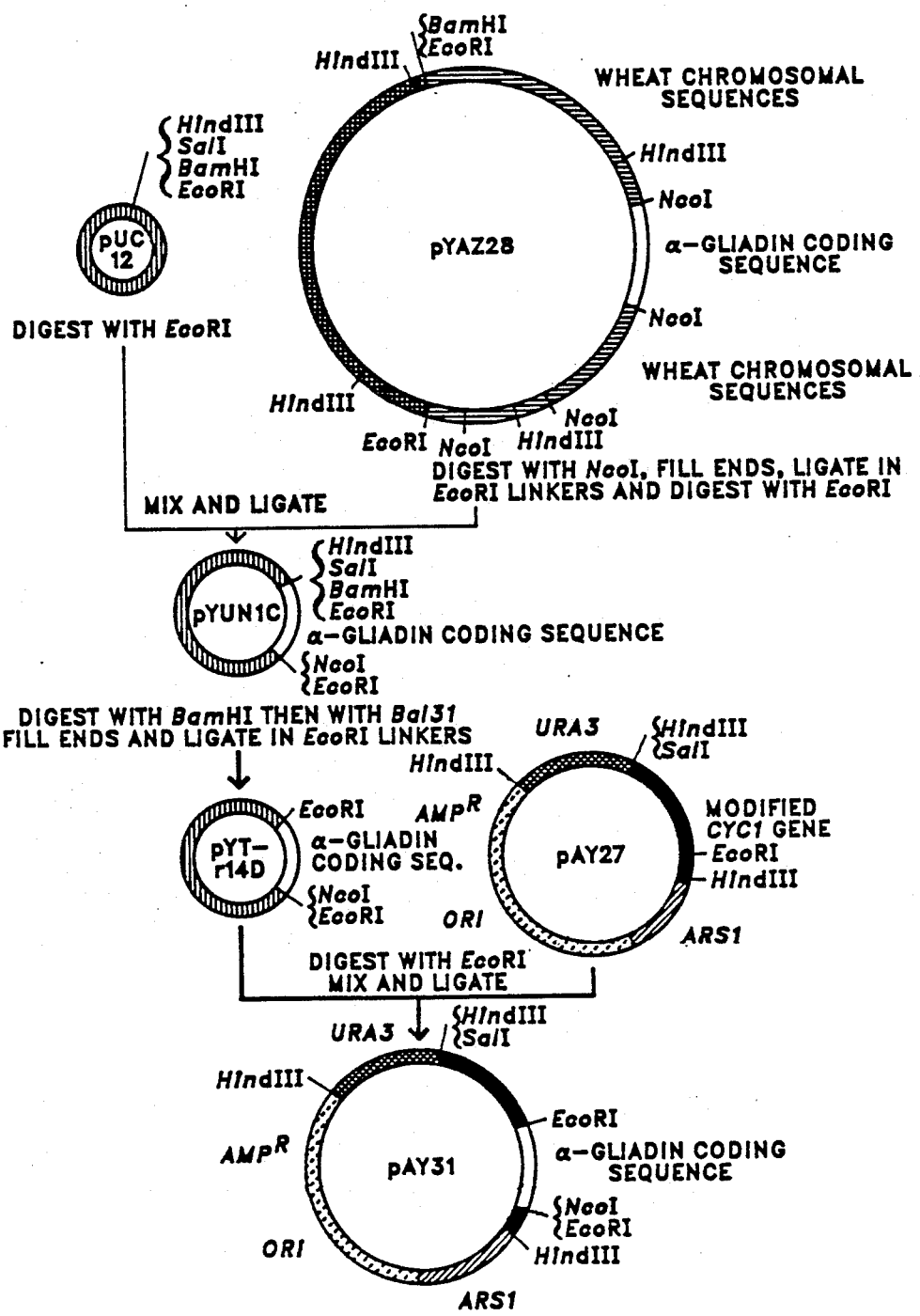
FIG. 2 is a schematic diagram of the construction of expression vector pAY31.

A portion of a cloned wheat gliadin gene was isolated and subcloned into the EcoRI site (expression site) of the expression vector pAY27 to produce a recombinant plasmid pAY31 capable of transforming yeast to uracil prototrophy and additionally capable of the production of wheat α-gliadin protein. The construction sequence is outlined in FIG. 2.

The starting wheat storage protein gene, α-1Y, was described by Anderson et al., *Nucleic Acids Research* 12: 8129–8144 (1984). A 6.2 kbp EcoRI fragment of this gene was cloned into the EcoRI site of plasmid RVI1Δ7 (Lynn et al, *Proc. Natl. Acad. Sci. U.S.A.* 80: 2656–2660 (1983)) to yield a 10.7 kbp plasmid, designated pYAZ28. pYAZ28 was digested with NcoI to release a 1025 bp fragment containing the 858 bp protein coding sequence, 113 bp of 5' and 54 bp of 3' flanking sequences. The ends were filled in with *E. coli* DNA polymerase I (Klenow fragment) ligated to EcoRI synthetic linkers, inserted into the EcoRI restriction site of pUC12 (Messing, *Meth. Enzymol.* 101: 20–78 (1983)) and transformed into *E. coli* K-12, JM103 (Δlac pro, thi, strA, supE, endA, sbcB15, hsdR4, F'traD36, proAB, lacIqZaM15) (Messing et al., *Nucleic Acids Research* 9(2): 309–321 (1981)). The resulting plasmid, designated pYUNIC, with the insert 5' end proximal to the BamHI restriction site in pUC12 was cleaved with BamHI and digested with Bal31, taking aliquots at intervals calculated to allow removal of most of the 5' flanking sequences. After Klenow fragment end-filling, addition of EcoRI linkers and religation, the truncated plasmids were transformed into *E. coli* JM103. Ampicillin resistant colonies were selected and the approximate extent of cleavage determined by sizing of PstI/EcoRI fragments on 7% polyacrylamide gels. The plasmid selected, designated as pYTr14D, was digested with EcoRI and the truncated α-gliadin fragment was transferred to bacteriophage M13mp10 (M13 bacteriophage with polylinker site in lacZ region (Messing et al., *Gene* 19: 269–276 (1982)) for deletion endpoint sequence analysis. The 5' flanking sequence was determined to begin 18 bp 5' to the ATG initiation codon and the 3' flanking sequence to end 54 bp 3' to the TGA termination codon, not counting EcoRI ends.

A second aliquot of the truncated α-gliadin gene fragment was ligated into the EcoRI site of pAY27. The ligation mixture was transformed into *E. coli* and the transformants were analyzed for the presence of the α-gliadin insert. Restriction endonuclease analysis was used to confirm that the insert was the α-gliadin gene and to determine its orientation in the vector. Digestion with PstI, and agarose gel electrophoresis confirmed that the α-gliadin gene is in the correct orientation for expression, i.e., such that the 5' flanking sequence of the wheat gluten protein gene fragment is proximal to the promoter of the modified CYC1 gene.

Figure 3:
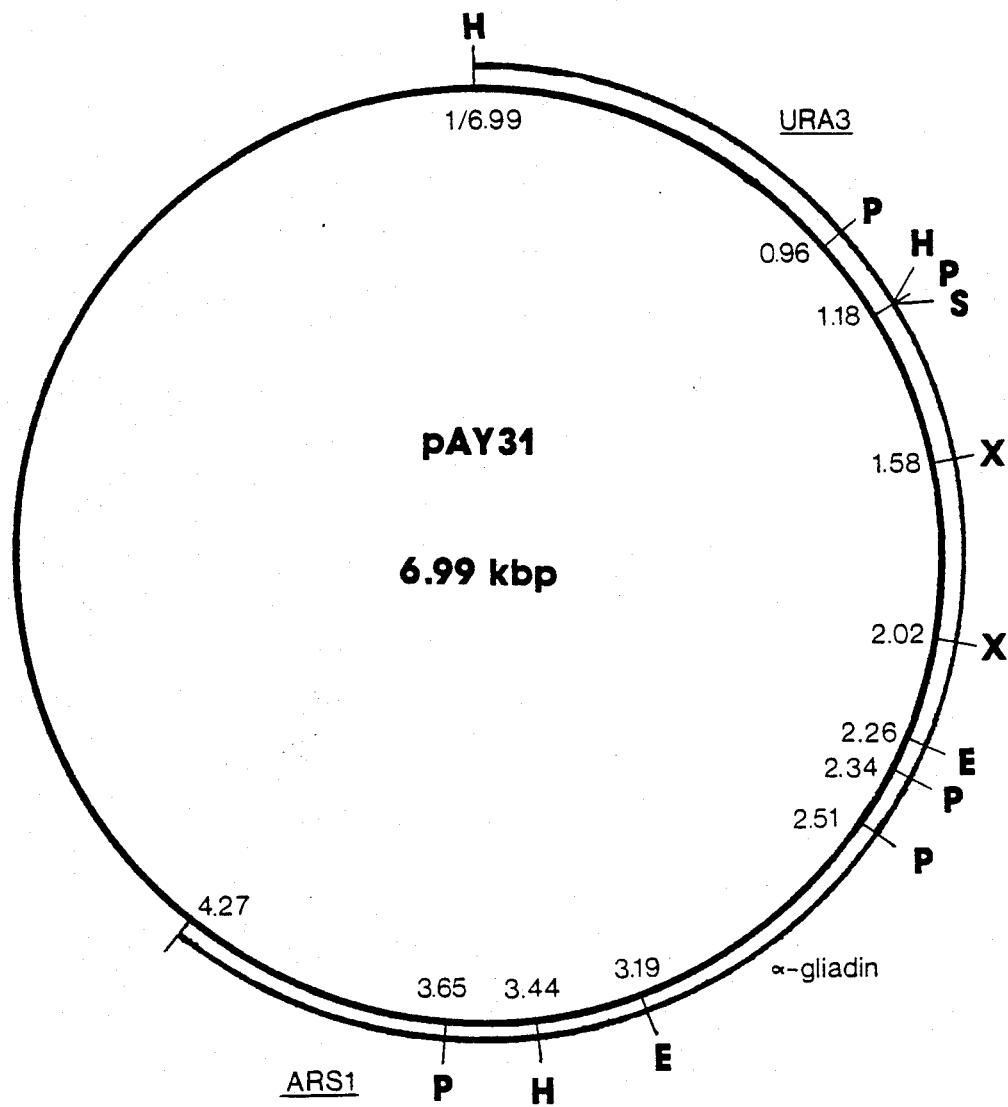
FIG. 3 shows restriction map of pAY31.

The restriction map of pAY31 is given in FIG. 3. Restriction sites are: E, EcoRI; H, HindIII; P, PstI; S, SalI; X, XhoI. The solid line indicates pUC8 sequences and the double lines indicate yeast sequences. The size of pAY31 is 6.99 kbp. The distances of the restriction sites are measured in kbp from the HindIII site at the junction of the pUC8 and yeast sequences. The nucleotide sequence of plasmid pAY31 is given in FIGS. 4A–4G. *E. coli* was transformed with pAY31 according to the method of Hanahan, supra. pAY31, contained in *E. coli*, is on permanent deposit with the culture collection of the Northern Regional Research Center (NRRL), Agricultural Research Service, U.S. Department of Agriculture, Peoria, Ill., and has been assigned the accession No. NRRL B-18121.

EXAMPLE 3

Preparation of Yeast Containing pAY31

The starting yeast, *S. cerevisiae* strain D1113-10B (MATΔ ura3-52 his3-a1 leu2-3,112 ilv3 can1-100 SUP4-o), was obtained from F. Sherman, Department of Biochemistry, University of Rochester School of Medicine. The yeast was maintained on YPD medium (2% peptone (Difco Laboratories, Inc. Detroit, Mi.), 2% dextrose, 1% yeast extract.

The yeast was transformed with the plasmid pAY31 by the alkaline cation method of Ito et al., *Journal of Bacteriology* 153: 163–168 (1983). The yeast was grown in 100 ml of YPD broth which had been inoculated with 1 ml of an overnight YPD culture followed by vigorous shaking to late log phase (OD600 of 1.6). Cells were collected by centrifugation at 1100×g for 5 minutes and were washed with 20 ml of TE buffer (10mM Tris-base, 1 mM disodium ethylenediaminetetraacetic acid (EDTA), pH 7.5). The cells were resuspended in 5 ml of TE buffer and a 500 ul aliquot of the cells was transferred to a 13×100 cm glass test tube that contained 500 $\mu$l of 200 mM lithium acetate (Sigma Chemical Co., St. Louis, Mo.). Following incubation at 30° C. for 1 hour with vigorous shaking, 100 $\mu$l of cells were transferred to a 1.5 ml polypropylene centrifuge tube containing 1 ug of pAY31 DNA in 15 of TE buffer. The tube was incubated statically at 30° C. for 30 minutes. An equal volume of 70% polyethylene glycol 8000 (PEG) in water was added and mixed thoroughly with a vortex mixer. After incubation at 30° C. for 1 hour, the cells were heat-shocked at 42° C. for 5 minutes, collected by centrifugation, and washed twice with sterile water. The cells were resuspended in 200 $\mu$l of water and plated on -ura omission medium plates to select for transformants containing pAY31.

The resulting population of cells is screened for uracil prototrophy by plating on agar medium permissive for the genotype MATα his3-Δ1 leu 2-3,112 ilv3. This media (uracil omission media) contains 0.67% bacto-yeast nitrogen base without amino acids, 2% dextrose, 2% bacto agar, distilled water, 20 mg/ml histidine, 80 mg/ml leucine, 30 mg/ml isoleucine, 150 mg/ml valine, and 20 mg/ml arginine HCl. Other media formulations which supply nitrogen, carbohydrates, minerals, and vitamins are also suitable for uracil prototrophic screening, provided they supply the above amino acids and lack uracil. Transformed yeast strain D1113-pAY31 is maintained on uracil omission media. D1113-pAY31 has been deposited with the NRRL culture collection, and has been assigned the accession No. Y-18402.

Transformed yeast colonies are grown in larger amounts in uracil media described above except without agar, with continuous shaking. Cells are collected for analysis of messenger RNA and protein similar to that of wheat gliadin. The temperature range for growth is about 22° to 32° C.; the preferred temperature is 30° C. Production of cells is obtained in about 18 to 24 hours. The pH range of the medium is about 5.4 to 6.0; the preferred pH is 5.6.

EXAMPLE 4

Analysis of the Expression of the u-gliadin Gene in Yeast

1. Isolation and Analysis of Yeast RNA

To assay for transcription of the α-gliadin insert, pAY27 and pAY31 were transformed into yeast strain D1113-10B and were plated on -ura omission medium plates. After incubation of 3 to 5 days, individual colonies were picked, grown, and total RNA was isolated as follows. Yeast transformed with either pAY27 or pAY31 were grown to a density of approximately $1 \times 10^7$ cells/ml in uracil omission medium at 30° C. with continuous shaking. Yeast were collected by centrifugation at 2500×g for 10 minutes at 0° C., and were resuspended in 5 ml of ice-cold 50 mM Tris-HCl (pH 8.0), 20 mM EDTA, and 1 M NaCl. Pre-cooled glass beads (0.5 mm dia.) were added to 80% of the volume of the liquid and the cells were disrupted by high-speed vortex mixing, three cycles of 30 seconds each, cooling the tube for 30 seconds on ice between vortexings. An equal volume of phenol: chloroform: isoamyl alcohol (50:49:1) was added and the extract was vortexed for three cycles of 30 seconds each. The extract was placed on ice for 30 seconds between vortexings. The phases were separated by centrifugation at 10,000×g for 10 minutes, and the aqueous phase was removed and re-extracted twice in the same manner. A final extraction was done with an equal volume of chloroform. The RNA was precipitated by the addition of 2.5 volumes of ethanol and maintained at −20° C. for three or more hours. Cells transformed by both plasmids were grown in -ura broth containing 10% dextrose or in -ura broth containing 3% glycerol and 0.1% dextrose, to cause repression and derepression, respectively, of the CYC1 promoter. The RNA from these cultures was analyzed by northern blot analysis for the presence of the α-gliadin:CYC1 hybrid mRNA transcript in the pAY31 transformed cells grown under the different conditions. The procedure for the northern blot analysis was as follows. Twenty micrograms of total cellular RNA was fractionated by electrophoresis on a 1.5% agarose gel containing 6% formaldehyde using 10 mM phosphate running buffer at pH 6.7 (Lehrach et al., *Biochemistry* 16: 4743–4751 (1977)). The RNA was blotted onto nitrocellulose membrane and probed by the procedure of Thomas, *Proc. Natl. Acad. Sci. U.S.A.* 77: 5201-5205 (1980) using a wheat α-gliadin gene fragment labeled with [$^{32}$P] by nick-translation. After washing and drying, the radioactive membrane areas were detected by exposure to x-ray film (Kodak XAR-5 or equivalent) with intensifying screens at −70° C. Total RNA isolated from D1113-10B that was transformed with pAY27 showed no specific hybridization from either treatment with the α-gliadin probe. However, the RNA isolated from the yeast transformed with pAY31 showed a distinct band of approximately 1050 bases in length, as detected by hybridization to the radioactive probe. This demonstrates synthesis of gliadin-specific RNA by the new yeast D1113-pAY31.

To demonstrate that transcription of the α-gliadin gene is under the control of the CYC1 promoter, gliadin plasmid pAY31 was transformed into *S. cerevisiae* strain WR3-R3, a yeast strain that contains a mutation in the hem1 locus that codes for δ-aminolevulenic acid synthase (Guarente and Mason, *Cell* 32: 1279-1286 (1983)), and which thus cannot synthesize the heme necessary to activate the CYC1 gene promoter that controls expression of the gliadin gene segment of the plasmid. Yeast transformed with pAY31 were grown in -ura omission medium containing Tween 80 and ergosterol to allow growth of the yeast and to completely repress the CYC1 promoters. The CYC1 promoters were derepressed by the addition of δ-aminolevulenic acid (ALA) to the medium when the cells had reached mid-log phase of growth. The RNA was purified from the cells at various times before and after addition of ALA to the medium and was analyzed by northern blot hybridization using the α-gliadin gene as the probe to determine the relative amounts of CYC1:α-gliadin mRNA present in each time period. Using this approach, gliadin-specific RNA was undetectable at the time of addition, was easily detectable after 5 minutes, and had reached near steady-state levels by 30 minutes after ALA addition. This analysis demonstrates that transcription of the α-gliadin gene is under the control of the CYC1 promoter.

To determine the structure of the message, the 3' end of the transcripts were nuclease mapped. A 600 bp MboI-HindIII DNA fragment containing the 3' end of the α-gliadin gene, its remaining 3' non-coding sequences, and the CYC1 transcription termination sequences was $^{32}$P-end-labeled at the MboI site within the u-gliadin coding sequences. When subjected to S1 nuclease the u-gliadin transcript protected a DNA fragment of 355±10 bases. The labeled MboI site is 313 bases from the termination codon of the α-gliadin gene, indicating a 3' non-coding region of the α-gliadin transcript of approximately 42±10 bases. This indicates that transcription is being terminated within the 3' non-coding L- sequences of the u-gliadin gene, about 150 bases 5' to the predicted transcription termination site.

2. Isolation and Analysis of Yeast Proteins

Western blot analysis was done to detect u-gliadin in total cellular protein extracts from transformed yeast. Yeast total proteins were prepared from *S. cerevisiae* D1113-10B transformed with plasmid pAY27 or pAY31. Yeast total cellular proteins were prepared from transformed yeast grown to a density of $1 \times 10^7$ cells/ml in uracil omission medium. The cells were collected by centrifugation at 5000×g for 10 minutes and were resuspended in 500 μl of 1 M sorbitol (pH 7.0). Zymolyase (125 μg) was added and the cell suspension was incubated at 37° C. for 1 hour. The cells were sedimented by centrifugation and were washed once with 500 μl of 1 M sorbitol. The pelleted cells were resuspended in 500 ul of Laemmli protein loading buffer (Laemmli, *Nature* 227: 680–685 (1970)) and placed in a boiling water bath for 3 minutes. The total cellular proteins were separated by sodium dodecyl sulfate (SDS)-polyacrylamide gel electrophoresis. Proteins were electrophoretically transferred to nitrocellulose membrane, essentially according to Towbin et al., *Proc. Natl. Acad. Sci. U.S.A.* 76: 4350–4354 (1979) except that the transfer buffer contained 10% methanol and 0.05% SDS. Transfers were carried out at 250 mA, at 10° C. Control experiments with α-gliadin indicated that greater than 80% transfer was achieved in 3 hours under these conditions. Antigen-antibody reactions were carried out according to Johnson and Elder, *J. Exp. Med.* 159: 1751–1756 (1983) using rabbit antiserum and prepared against a purified u-gliadin fraction (Greene, *Plant Physiology* 68: 778–783 (1981)). Bands of gliadin-complexed antibody were detected by binding [$^{125}$I]-*Staphylococcus aureus* protein A, followed by x-ray film exposure-and analysis, as described for RNA, above. Using α-gliadin specific rabbit antibody as a probe, a single protein band was detected by immunoblot analysis of extracts from yeast D1113-pAY31. This band migrated with an apparent molecular size of 31 kDa in a 12% gel; and co-migrated with the smaller 32 kDa size class of the gliadin fraction used to raise the antiserum. Extracts of yeast D1113-pAY27 (expression vector only) were gliadin-negative by this analysis.

The behavior of the yeast-synthesized protein is more consistent with the 30.8 kDa size predicted from the gene sequence (Anderson et al., supra) for mature α-gliadin than with the 32.9 kDa size predicted for the α-gliadin precursor. These results suggest that an α-gliadin precursor is produced in the yeast D1113-pAY31 and processed to a mature protein of the same size as u-gliadin synthesized in wheat. By densitometric comparison to the α-gliadin control bands in the autoradiogram, with the assumption that all components of the sensitizing u-gliadin fraction have the same antigenicity, the yeast-synthesized gliadin was calculated to compose approximately 0.1% of the total D1113-pAY31 protein. The yeast gliadin band exhibited no streaking with very long autoradiographic film exposure, which indicates high stability in the transformed yeast cell.

EXAMPLE 5

Preparation of Yeast Capable of Producing β-gliadin

Production of a yeast strain capable of producing β-gliadin is carried out by construction wheat β-gliadin plasmid, pAY32 which is identical to pAY31 with the exception that a 1016 base pair β-gliadin gene segment of the sequence shown in FIG. 5A and 5B is inserted between positions 2698 and 3630 in place of the 932 bp base pair α-gliadin gene segment. Next, pAY32 is transformed in yeast as described in Example 3.

The specifics of the construction are as follows:

Plasmid pCZR108, which contains a 7650 bp segment of gliadin gene CY10, is digested sequentially with restriction enzymes HaeIII and XbaI, and the resulting fragments separated by electrophoresis in an agarose gel. A 1606 bp fragment, containing the protein coding sequences, 94 base pairs of 5' flanking sequence and 572 base-pairs of 3' flanking sequence, is recovered from the gel, purified and ligated into the SmaI restriction site of plasmid pUC8 to yield pβG10. pBG10 is transformed into *E. coli*, amplified, and recovered.

Next, pβG10 is cleaved with restriction enzyme BclI, at a position 81 base-pairs 5' to the translation initiation codon ATG and digested with exonuclease Bal-31 to a position 16-21 base-pairs 5' to the ATG. The treated plasmid is digested with *E. coli* DNA polymerase (Klenow fragment) to convert the ends to a flush, or "blunt" state. A linker oligonucleotide, containing the EcoRI restriction site is ligated to the plasmid ends with T4 ligase, cleaved with restriction enzyme EcoRI, and religated to yield pβG101, which is transformed into *E. coli*, amplified, and recovered.

pβG101 is cleaved with restriction enzyme SpeI, at a position 119 bp 3' to the translation stop codon TGA and digested with Bal-31 to a position 54–59 bp 3' to the TGA. It is then converted to a blunt-ended state, an EcoRI restriction site added as above, cleaved with EcoRI, and the two resulting DNA fragments separated by agarose gel electrophoresis. The smaller fragment would be approximately 1025 bp in length, and contain, between EcoRI-cohesive ends, the 930 bp β-gliadin gene coding sequence, approximately 19 bp of 5' flanking sequence, the TGA stop codon and approximately 56 base-pairs of 3' flanking sequence. The smaller fragment is recovered from the gel, purified, and ligated into the expression vector pAY27 to yield plasmids pAY32 and pAY32R, which differ only in the orientation of the β-gliadin insert relative to the CYC1 gene promoter.

Several individual colonies of pAY32/32R-transformed E. coli are grown in small-scale cultures, plasmid DNA isolated, and digested with restriction enzyme PstI to identify those that contain pAY32, in which the 5' flanking sequence of the β-gliadin gene segment is proximal to the CYC1 gene promoter. The digested pAY32 would include fragments approximately 1160, 1240, and 170 bp in length. Plasmid pAY32 is isolated and used to transform yeast D1113-10B to uracil prototrophy, as described above, to yield β-gliadin producing strain D1113-pAY32.

By analogous procedures, a segment of wheat glutenin gene CYλ5 is inserted into pAY27 to yield glutenin recombinant plasmid pAY33 which, when transformed into yeast D1113-10B, results in D1113-pAY33, a yeast stain capable of synthesizing a glutenin protein. This general approach allows the production of yeast strains capable of synthesizing any gluten protein for which a gene is available.

It is understood that the foregoing detailed description is given merely by way of illustration and that modification and variations may be made therein without departing from the spirit and scope of the invention.

Having thus described our invention, we claim:

1. A wheat gluten protein gene plasmid, comprising:
   (a) an E. coli plasmid pUC8 wherein the EcoRI site has been removed;
   (b) autonomously replicating yeast sequence ARS1;
   (c) a yeast UEA3 gene;
   (d) a modified yeast iso-1-cytochrome c gene retaining a promoter region and transcription termination sequence, and wherein protein coding sequences have been deleted and replaced with a synthetic EcoRI restriction site;
   (e) a wheat gluten protein gene fragment which has an amino acid coding region which upon expression results in a wheat gliadin or glutenin protein, translation initiation and termination sequences, and 3' and 5' flanking nucleotide sequences, but excluding transcription initiation and termination sequences, said gene fragment being cloned into said EcoRI site of said modified CYC1 gene.

2. The plasmid according to claim 1 wherein said wheat gluten protein gene fragment codes for α-gliadin.

3. The plasmid according to claim 1 wherein said wheat gluten protein gene fragment codes for α-gliadin.

4. The plasmid according to claim 1 wherein said wheat gluten protein gene fragment codes for glutenin.

5. The plasmid according to claim 2, wherein the plasmid is pAY31.

6. An Escherichia coli strain transformed with the plasmid of claim 1.

7. The Escherichia coli strain of claim 6 wherein the plasmid used for transformation is pAY31.

8. Saccharomyces cerevisiae yeast transformed with the plasmid of claim 1.

9. The yeast according to claim 8 wherein said plasmid is pAY31.

10. A method of preparing a wheat gluten protein gene plasmid, comprising ligating a wheat gluten protein gene fragment which has an amino acid coding region which upon expression results in a wheat gliadin or glutenin protein, translation initiation and termination sequences, and 3' and 5' flanking nucleotide sequences, but does not have transcription initiation and termination sequences, into an expression vector comprising (a) an E. coli plasmid pUC8 wherein the EcoRI site has been removed; (b) autonomously replicating yeast sequence ARS1; (c) a yeast URA3 gene; and (d) a modified yeast iso-1-cytochrome c (CYC1) gene retaining a promoter region and transcription termination sequence, and wherein protein coding sequences have been deleted and replaced with a synthetic EcoRI restriction site; and ligating occurring in said EcoRI site of said expression vector in an orientation such that the 5' flanking sequence of the wheat gluten protein gene fragment is proximal to the promoter of the modified CYCI gene.

11. A method of preparing a strain of yeast capable of synthesizing wheat gluten protein, which comprises transforming a strain of S. cerevisiae yeast with said wheat gluten protein gene plasmid of claim 1 whereby synthesis of wheat gluten protein coded by said plasmid occurs during the growth and replication of said transformed yeast under normal culture conditions.

12. A method of producing wheat gluten protein from yeast, comprising cultivating said yeast of claim 8 in uracil omission medium at a temperature of about 22° to 32° C. until a recoverable quantity of wheat gluten protein is produced.

13. The method of claim 12 wherein said yeast is D1113-pAY31.

* * * * *

UNITED STATES PATENT AND TRADEMARK OFFICE
CERTIFICATE OF CORRECTION

PATENT NO. : 4,826,765

DATED : May 2, 1989

INVENTOR(S) : Frank C. Greene et al.

It is certified that error appears in the above—identified patent and that said Letters Patent is hereby corrected as shown below:

In column 3, line 36, delete " α-gliadin" and insert -- β-gliadin --.
In column 7, line 24, delete "eectrophoresed" and insert -- electrophoresed --.
In column 8, line 29, delete "pYUNIC" and insert -- pYUN1C --.
In column 9, line 11, delete "MATΔ" and insert -- MATα --.
In column 9, line 11, delete "his3-al" and insert -- his3-Δ1 --.
In column 10, line 3, delete "u-gliadin" and insert -- α-gliadin --.
In column 11, lines 26-27, delete "u-gliadin" and insert -- α-gliadin --.
In column 11, line 28, delete "u-gliadin" and insert -- α-gliadin --.
In column 11, line 34, delete "L-" before sequences.
In column 11, line 34, delete "u-gliadin" and insert -- α-gliadin --.
In column 11, line 38, delete "u-gliadin" and insert -- α-gliadin --.
In column 12, line 18, delete "u-gliadin" and insert -- α-gliadin --.
In column 12, line 21, delete "u-gliadin" and insert -- α-gliadin --.

UNITED STATES PATENT AND TRADEMARK OFFICE
CERTIFICATE OF CORRECTION

PATENT NO. : 4,826,765

DATED : May 2, 1989

INVENTOR(S) : Frank C. Greene et al.

It is certified that error appears in the above—identified patent and that said Letters Patent is hereby corrected as shown below:

```
In claim 1, line 5, delete "UEA3" and insert -- URA3 --.
In claim 1, line 6, before "gene" insert -- (CYC1) --.
In claim 3, line 2, delete " α-gliadin" and insert
--  β-gliadin --.
In claim 10, line 16, delete "and" and insert -- said --.
```

Signed and Sealed this

Sixth Day of March, 1990

Attest:

JEFFREY M. SAMUELS

Attesting Officer

Acting Commissioner of Patents and Trademarks